United States Patent
Dewey

(10) Patent No.: US 8,262,734 B2
(45) Date of Patent: *Sep. 11, 2012

(54) STACKABLE INTERVERTEBRAL DEVICES AND METHODS OF USE

(75) Inventor: Jonathan M. Dewey, Raleigh, NC (US)

(73) Assignee: Warsaw Orthopedic, Inc, Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/111,690

(22) Filed: May 19, 2011

(65) Prior Publication Data

US 2011/0282455 A1 Nov. 17, 2011

Related U.S. Application Data

(63) Continuation of application No. 11/945,813, filed on Nov. 27, 2007, now Pat. No. 7,967,866.

(51) Int. Cl.
*A61F 2/44* (2006.01)
(52) U.S. Cl. ............ 623/17.15; 606/90; 623/17.17
(58) Field of Classification Search .... 623/17.11–17.16; 606/90
See application file for complete search history.

(56) References Cited

U.S. PATENT DOCUMENTS

| | | | | |
|---|---|---|---|---|
| 6,387,130 B1* | 5/2002 | Stone et al. | ............ | 623/17.16 |
| 2003/0130739 A1* | 7/2003 | Gerbec et al. | ............ | 623/17.15 |
| 2006/0058876 A1* | 3/2006 | McKinley | ............ | 623/17.11 |
| 2006/0122701 A1* | 6/2006 | Kiester | ............ | 623/17.11 |
| 2006/0189999 A1* | 8/2006 | Zwirkoski | ............ | 606/90 |
| 2008/0281425 A1* | 11/2008 | Thalgott et al. | ............ | 623/17.16 |
| 2009/0005870 A1* | 1/2009 | Hawkins et al. | ............ | 623/17.11 |
| 2009/0157186 A1* | 6/2009 | Magerl | ............ | 623/17.16 |
| 2010/0280617 A1* | 11/2010 | Coppes et al. | ............ | 623/17.16 |

* cited by examiner

*Primary Examiner* — Eduardo C Robert
*Assistant Examiner* — Lynnsy Schneider

(57) ABSTRACT

An intervertebral device for spacing apart vertebral members comprises a plurality of stackable shims including at least a first shim and a second shim. The first shim includes a first body with a first portion of a male-female connector, and a removable guide that is affixed to the first body and extends along at least a portion of the first body. The second shim includes a second body with a second portion of the male-female connector. A longitudinal passage extends through the second body and is sized to receive the guide on the first body. The second shim is moveable relative to the first shim with the guide disposed in the passage between a disengaged position and an engaged position. In the engaged position, the first shim is stacked on the second shim.

17 Claims, 10 Drawing Sheets

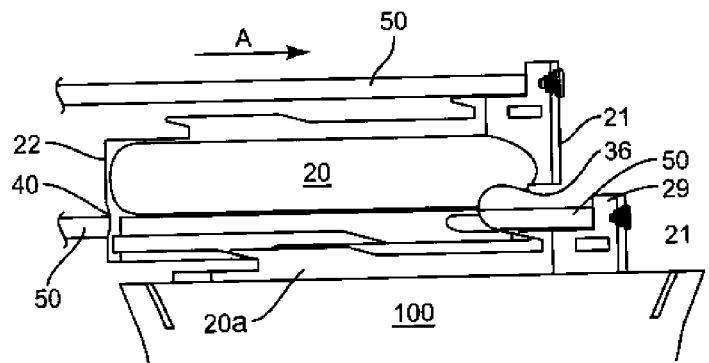 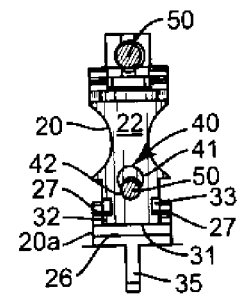
FIG. 11A  FIG. 11B
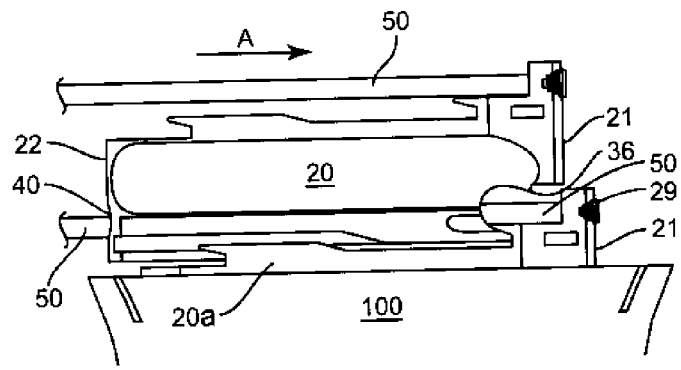 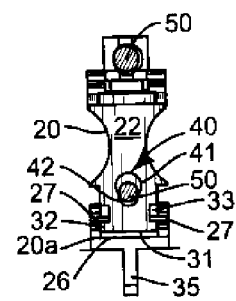
FIG. 12A  FIG. 12B
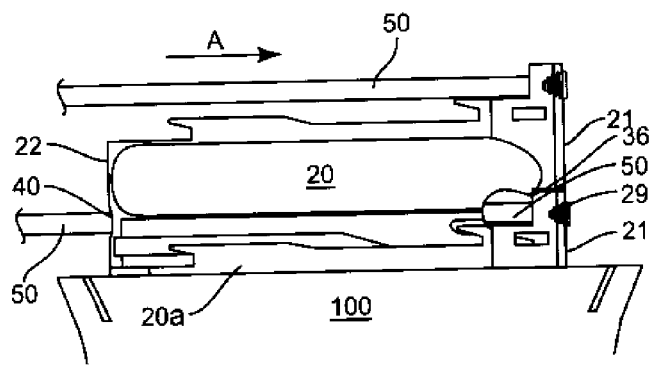 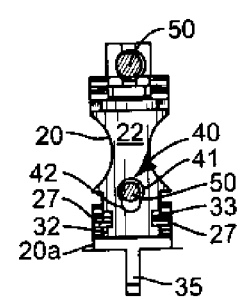
FIG. 13A  FIG. 13B

STACKABLE INTERVERTEBRAL DEVICES AND METHODS OF USE

REFERENCE TO RELATED APPLICATION

The present application is a continuation of application Ser. No. 11/945,813, filed on Nov. 27, 2007now U.S. Pat. No. 7,967,866, which is herein incorporated by reference in its entirety.

BACKGROUND

The present application is directed to an interbody device to space vertebral members and, more particularly, to devices constructed of a plurality of shims that are individually inserted between the vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants may reduce or eliminate the pain and neurological deficit, and may increase the range of motion.

SUMMARY

The present application is directed to implants for spacing vertebral members. One embodiment includes a first shim with a distal end and an opposing proximal end. The implant also includes a guide rod with an elongated shape with a distal end and an opposing proximal end with the distal end mounted at the distal end of the first shim. The guide rod has a greater length measured between the distal and proximal ends than the first shim with the proximal end of the guide rod proximally extending outward beyond the proximal end of the first shim. The implant also includes a second shim stacked on the first shim. The second shim has a longitudinal passage that is fully circumferentially enclosed by the second shim with the guide rod disposed in the passage and extending entirely therethrough.

Another implant includes a first shim that extends along a first longitudinal axis from a proximal end to a distal end. The first shim also has a first center between the ends, and a ramp. The implant includes a second shim that extends along a second longitudinal axis from a proximal end to a distal end. The second shim has a second center between the ends and a contact section. The second shim is configured to be slidable relative to the first shim between first and second configurations. The first configuration includes the second center located distally of the first shim proximal end and disposed relatively farther from the first shim distal end, and the second configuration includes the second center located relatively closer to the first shim distal end. The ramp and the contact section are configured for longitudinal sliding with a distance measured between the longitudinal axes being smaller in the second configuration than in the first configuration.

Another implant includes a first shim with a distal end and an opposing proximal end with a first longitudinal axis extending through the ends. The implant includes a guide rod with an elongated shape with a distal end and an opposing proximal end, with the distal end of the guide rod mounted at the distal end of the first shim. The guide rod has a greater length measured between the distal and proximal ends than the first shim with the proximal end of the guide rod proximally extending outward beyond the proximal end of the first shim. The implant includes a second shim with a distal end and a proximal end. The second shim also includes a longitudinal passage that is fully circumferentially enclosed by the second shim and a contact section. The guide rod is disposed in the passage and extends entirely therethrough. The second shim is configured to be slidable relative to the first shim and along the guide rod between a first configuration with the second shim positioned on the first shim by a first amount and a second configuration with the second shim positioned on the first shim by a larger second amount. A distance measured between the longitudinal axes being smaller in the second configuration than in the first configuration.

BRIEF DESCRIPTION OF THE DRAWINGS

FIG. 11A is a side view of a second shim being inserted into an intervertebral space according to one embodiment.

FIG. 11B is an end view of the second shim and the end shim of FIG. 11A.

FIG. 12A is a side view of a second shim being inserted into an intervertebral space according to one embodiment.

FIG. 12B is an end view of the second shim and the end shim of FIG. 12A.

FIG. 13A is a side view of a second shim seated with a first shim in an intervertebral space according to one embodiment.

FIG. 13B is an end view of the second shim and the end shim of FIG. 13A.

DETAILED DESCRIPTION

Figure 1:
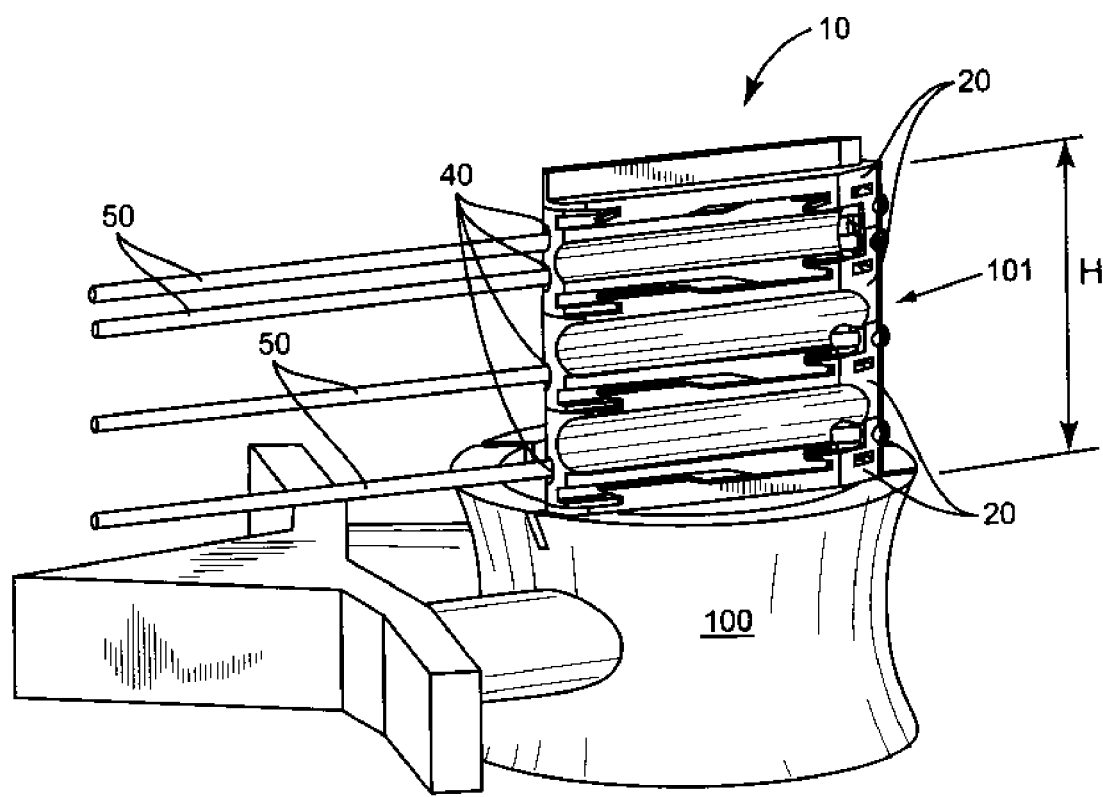
FIG. 1 is a perspective view of a device with attached guides according to one embodiment.

The present application is directed to an intervertebral device 10 to space apart vertebral members. FIG. 1 illustrates one embodiment of the device that includes two or more shims 20 placed together in a stacked configuration in an intervertebral space 101. The stacked configuration gives the device 10 an overall height H to space apart the vertebral members 100. The shims 20 are aligned relative to each other with a passage 40 of a second shim 20 engaging a guide 50 of a first shim 20. The shims 20 are individually inserted into the intervertebral space 101 and stacked together to attain the desired height H for spacing the vertebral members 100. Once the desired height H is attained, the guides 50 may be removed, with only the shims 20 remaining in the intervertebral space 101 (see FIG. 17).

Figure 2:
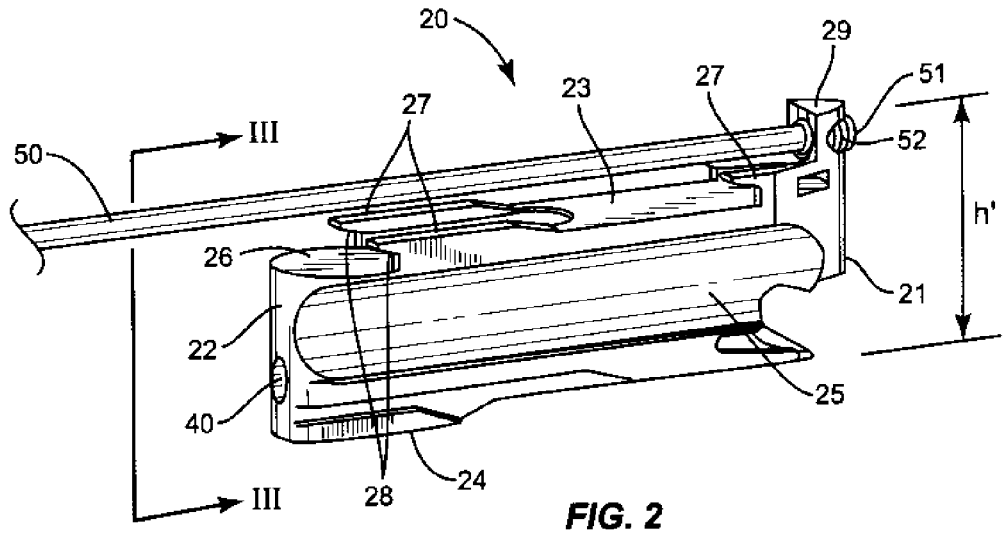
FIG. 2 is a perspective view of a shim with an attached guide according to one embodiment.
Figure 3:
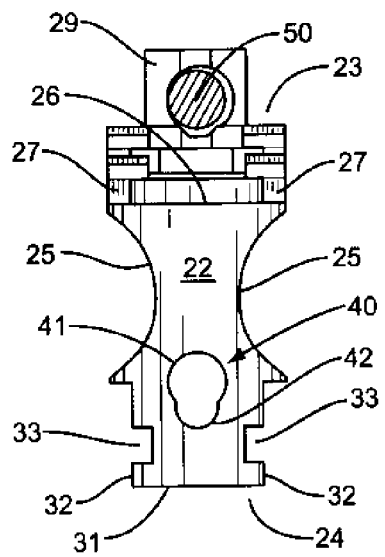
FIG. 3 is an end view of the shim and attached guide of FIG. 2.

One embodiment of a shim 20 with an attached guide 50 is illustrated in FIGS. 2 and 3. Shim 20 includes first and second ends 21, 22, first and second sides 23, 24, and lateral sides 25. In this embodiment, shim 20 includes an elongated, narrow shape with a major axis extending through the first and second ends 21, 22, and a minor axis extending through the lateral sides 25. The first end 21 may include a rounded shape to facilitate insertion through soft tissue and into the intervertebral space 101. The shim 20 further includes a height h' measured between the first and second sides 23, 24.

The first side 23 includes a substantially flat contact surface 26 positioned between a pair of rails 27. Rails 27 extend beyond the contact surface 26 and together form a portion of a male-female connector to receive an adjacent shim 20 as will be explained in detail below. Rails 27 may extend along the entirety or discrete sections of the first side 23. FIG. 2 illustrates the rails 27 extending along discrete sections of the first side 23 with the rails 27 beginning at a point spaced away from the second end 22 and extending a limited length towards the first end 22. Ramps 28 may be positioned at the end of the rails 27. Ramps 28 may include an angled surface that facilitates engagement with a subsequent shim 20. The first and second sides 23, 24 are also constructed to prevent lateral movement or tipping of the shim 20 within the intervertebral space 101. In one embodiment, ends of the first and second sides 23, 24 include enlarged widths to increase the contact area with adjacent shims 20 or the vertebral members 100.

The first side 23 further includes an engagement block 29 configured to receive and engage with the guide 50. The engagement block 29 extends upward above the contact surface 26. An opening 30 is formed in the engagement block 29 to receive the guide 50. In one embodiment, both the opening 30 and guide 50 are threaded. Guide 50 may attach to the shim 20 at a variety of different locations. In the embodiment of FIG. 2, the guide 50 attaches at the first end 21. In another embodiment, the guide 50 attaches at the second end 22.

The second side 24 is configured to engage with the first side 23 of an adjacent shim 20. A contact surface 31 is substantially flat and configured to engage with the contact surface 26. Tabs 32 extend outward and forms gaps 33 sized to engage with the rails 27.

In one embodiment as illustrated in FIGS. 2 and 3, the first and second sides 23, 24 are substantially parallel. The shims 20 may also come in different heights that may be used in a variety of combinations to build the overall height H of the device 10. By way of example, a first shim 20 may include a height of about 10 mm, and another shim 20 may include a height of about 25 mm. In one embodiment, the sides 23, 24 are positioned at an angle to match the curvature of the spine. In one specific embodiment, the angle matches the lordotic curvature of the spine. Further, the height h' of the shim 20 may be substantially constant or may vary along the length.

In one embodiment, the shim 20 is adjustable to set the height h' as necessary for the specific use. The shim 20 may include an adjustment mechanism, such as a threaded connection between first and second sections, or a ratcheting mechanism. The adjustment mechanism may provide for setting the height h' either prior to or after insertion into the intervertebral space 101.

The passage 40 extends through the shim 20 and is sized to receive the guide 50 of an adjacent shim 20. The passage 40 generally extends between the first and second ends 21, 22. The passage 40 may extend through an entire length of the shim 20 from the first end 21 to the second end 22, or may extend through a limited length. In one embodiment, the passage 40 is substantially parallel with the contact surfaces 26, 31. FIG. 3 illustrates an embodiment of the passage 40 with an enlarged section 41 with a first width and a reduced section 42 with a smaller width. Other embodiments feature the passage 40 with a variety of shapes including but not limited to circular, oval, and rectangular.

Figure 4:
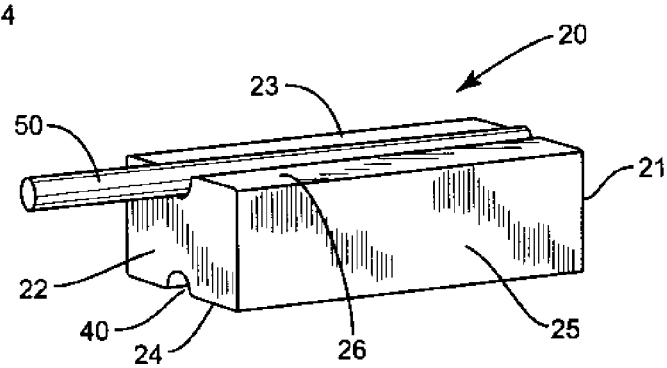
FIG. 4 is a perspective view of a shim with an attached guide according to one embodiment.

The guide 50 is attached to and extends outwardly from the shim 20. Guide 50 provides a structure for aligning shims 20 subsequently introduced into the intervertebral space 101 with a previously introduced shim 20. As illustrated in FIG. 2, guide 50 includes an elongated shape. The size and shape of the guide 50 may be substantially constant along the length, or may vary. In one embodiment, the length of the guide 50 is greater than the shim 20. A first end 51 of the guide 50 is removably attached to the shim 20. Various methods for attachment may be used, including but not limited to threads 52 that engage with the threaded opening 30 on the shim 20, a friction fit, and a ball-and-detent arrangement. The removable attachment allows for the guide 50 to be removed from the shim 20 after insertion into the intervertebral space 101. In another embodiment, the guide 50 is cut away from the shim 20 after being inserted into the intervertebral space 101. In this embodiment, a portion of the guide 50 may remain attached to the shim 20 and permanently remain within the intervertebral space 101. In one embodiment as illustrated in FIGS. 2 and 3, the guide 50 is positioned above the contact surface 26 such that a space is formed between the guide 50 and surface 23. In another embodiment as illustrated in FIG. 4, guide 50 is positioned at the contact surface 26.

Guide 50 may be constructed from a variety of materials, including but not limited to stainless steel, titanium, Nitinol, and polymers. In one embodiment, guide 50 is rigid and able to support the shim 20. Guide 50 forms a handle for the surgeon to grasp to manipulate to insert the shim 20 into the intervertebral space 101 in addition to providing an alignment path for subsequent shims 20. In one embodiment, the guide 50 includes a rectangular cross-sectional shape. This shape allows rotational stability during insertion and prevents buckling of the guide 50 when used as an insertion tool for positioning the shim 20 within the intervertebral space 101. In another embodiment, guide 50 is constructed of a flexible material that is not adequate to support the shim 20 during insertion into the intervertebral space 101.

Shims 20 may include a variety of shapes and sizes. FIG. 4 illustrates an embodiment with the shim 20 including a substantially rectangular shape. Guide 50 is positioned in a cutout 34 in the superior side 23. The passage 40 on the inferior side 24 is partially exposed to receive the guide 50.

Figure 5:
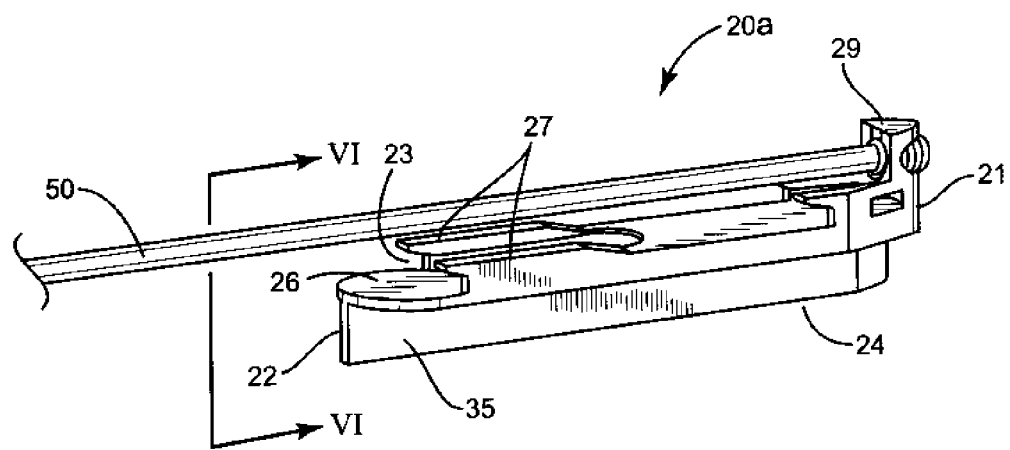
FIG. 5 is a perspective view of an end shim with an attached guide according to one embodiment.
Figure 6:
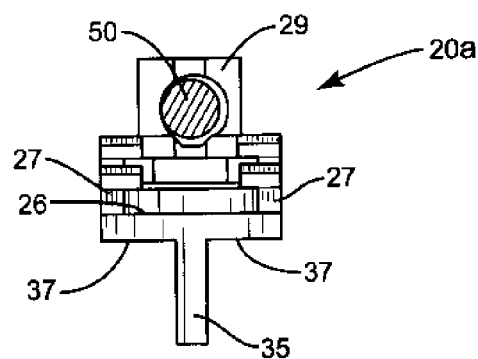
FIG. 6 is an end view of the end shim and the attached guide of FIG. 5.
Figure 7:
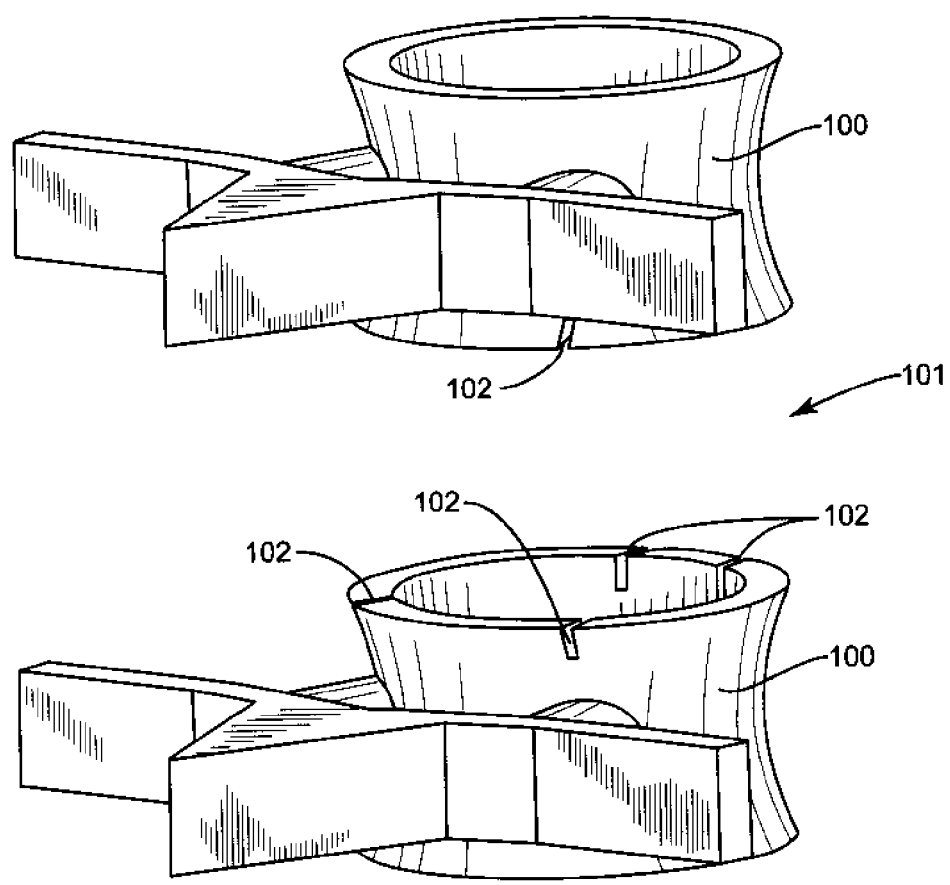
FIG. 7 is a perspective view of an intervertebral space formed between vertebral members according to one embodiment.

One type of shim 20 is an end shim 20a illustrated in FIGS. 5 and 6. End shims 20 are positioned in the intervertebral space 101 and directly contact one of the vertebral members 100. End shims 20a include a keel 35 on the second side 24. The keel 35 provides additional engagement and stability between the shim 20a and the vertebral member 100. Keel 35 may extend the entire length of the shim 20, or a limited distance along the length. The keel 35 is sized to fit in a trough 102 formed in the vertebral member 100 as will be explained below. In one embodiment, the keel 35 may include a sharpened leading edge and/or outer edge that acts as a cutting instrument to form the trough 102 in the vertebral member 100. The end shims 20a may also be used for distraction and manipulation of the vertebral members 100.

A support surface 37 is spaced from the outer edge of the keel 35. Support surface 37 contacts against the vertebral member 100 when the keel 35 is in the trough 102. The first side 23 is configured to engage with shims 20 in a stacked orientation. First side 23 may include various connectors, including rails 27 and a contact surface 26 as illustrated in FIGS. 5 and 6. In one embodiment, a height of the end shims 20a is less than a height of the intermediate shims 20.

FIGS. 7-17 illustrate one method of inserting the device 10 into the intervertebral space 101 between the vertebral members 100. In this embodiment, a corpectomy procedure has been performed to form the intervertebral space 101. Initially, troughs 102 may be formed in one or both of the vertebral members 100. Troughs 102 extend across a section or entirety of the vertebral members 100 and are sized to receive the keels 35 on the end shims 20a.

Figure 8:
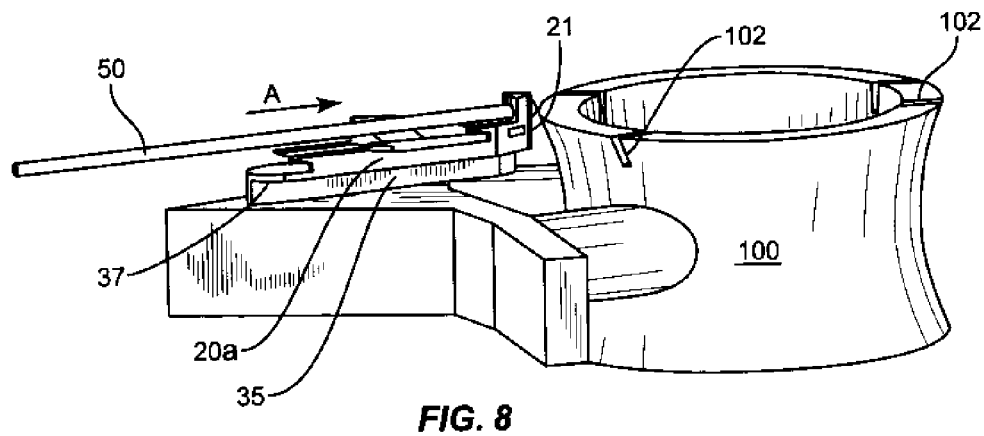
FIG. 8 is a perspective view of an end shim being inserted into an intervertebral space according to one embodiment.
Figure 9:
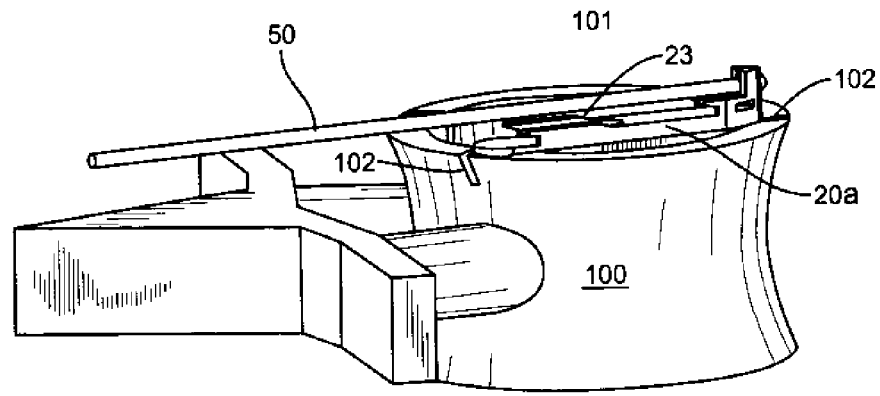
FIG. 9 is a perspective view of an end shim in an intervertebral space according to one embodiment.

FIG. 8 illustrates a first end shim 20a being inserted into the intervertebral space 101 in the direction of arrow A. During insertion, the keel 35 at the first end 21 is initially aligned with the trough 102 with the support surface 37 abutting against the face of the vertebral member 100. FIG. 9 illustrates the end shim 20a fully inserted in the intervertebral space 101. The end shim 20a is positioned with the first side 23 faces away from the inferior vertebral member 10 and into the intervertebral space 101 in a position to engage a subsequent shim. Further, the guide 50 remains affixed to the end shim 20a and extends outward from the intervertebral space 101 to receive and align the subsequent shim.

Figure 10:
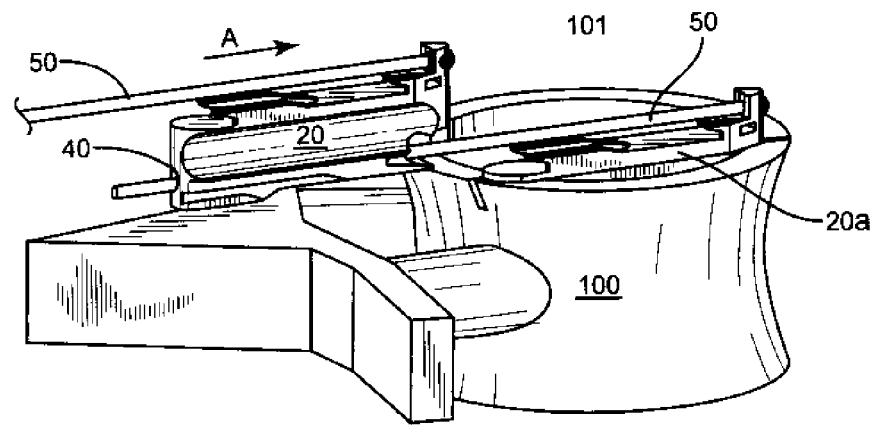
FIG. 10 is a perspective view of a second shim being inserted into an intervertebral space according to one embodiment.

FIG. 10 illustrates the subsequent shim 20 or second shim being inserted into the intervertebral space 101. During insertion, the guide 50 of the end shim 20a is received in the passage 40 on the second shim 20 while the second shim 20 remains away from the intervertebral space 101. The second shim 20 is moved in the direction of arrow A with the passage 40 sliding along the guide 50.

FIG. 11A illustrates a side view and FIG. 11B an end view of the second shim 20 partially engaged with the end shim 20a. As the shim 20 begins to overlap shim 20a, engagement mechanisms on each begin to interlock the shims 20, 20a. Specifically, the tabs 32 and gaps 33 on the second side 22 of the second shim 20 engage the rails 27 on the end shim 20a. As illustrated in FIG. 11B, the contact surface 31 on the second shim 20 remains spaced away from the contact surface 26 on end shim 20a.

FIGS. 12A and 12B illustrates the second shim 20 more fully engaged with the end shim 20a. Second shim 20 has moved laterally a further amount in the direction of arrow A. Further, the tabs 32 on the second shim 20 continue to slide along the rails 27 on the end shim 20a. In this embodiment, rails 27 include a downward slope such that the further lateral movement of the second shim 20 relative to end shim 20a closes the gap between the contact surfaces 26, 31. As illustrated in FIG. 12B, the gap between the surfaces 26, 31 has been reduced from the previous size of FIG. 11B. Further, guide 50 of end shim 20a begins to move out of the reduced section 42 of passage 40 and into the enlarged section 41 as the second shim 20 moves towards closer proximity with shim 20a.

The lateral movement of the shim 20 may result in axial movement of the shim 20 in the intervertebral space 101. The amount of axial movement may be coordinated to control the overall height H of the device 10. In one embodiment, the rails 27 include a downward slope such that the shim 20 moves downward during insertion. In another embodiment, the shim 20 may move away from the shim 20a during insertion. In both of these embodiments, the shim 20 provides distraction of the intervertebral space 101. In another embodiment, the shim 20 is structured for the lateral movement into the intervertebral space 101 to cause substantially parallel movement of the shim 20 relative to shim 20a (i.e., no downward movement of shim 20 towards shim 20a). An instrument (not illustrated) may also be used to facilitate insertion of the shim 20 into the intervertebral space 101.

FIGS. 13A and 13B illustrate the second shim 20 fully engaged and interlocked with the end shim 20a. The contact surfaces 26, 31 are in contact with no spaces formed therebetween. Further, the guide 50 is fully positioned in the enlarged section 41 of passage 40. In one embodiment, the engagement mechanisms of the shims 20, 20a include a locking structure to prevent further lateral movement of shim 20 relative to shim 20a. In one embodiment, second shim 20 includes a face 36 that abuts against the engagement block 29 on the end shim 20a to prevent further lateral movement in the direction of arrow A. Further movement in the direction opposite to arrow A may be prevented by a variety of structures including but not limited to the indents on the rails 27 that engage with the tabs 32, and a ball-and-detent mechanism on the shims 20, 20a, a one-way ratchet, lateral locking tabs, and friction clutches.

Figure 14:
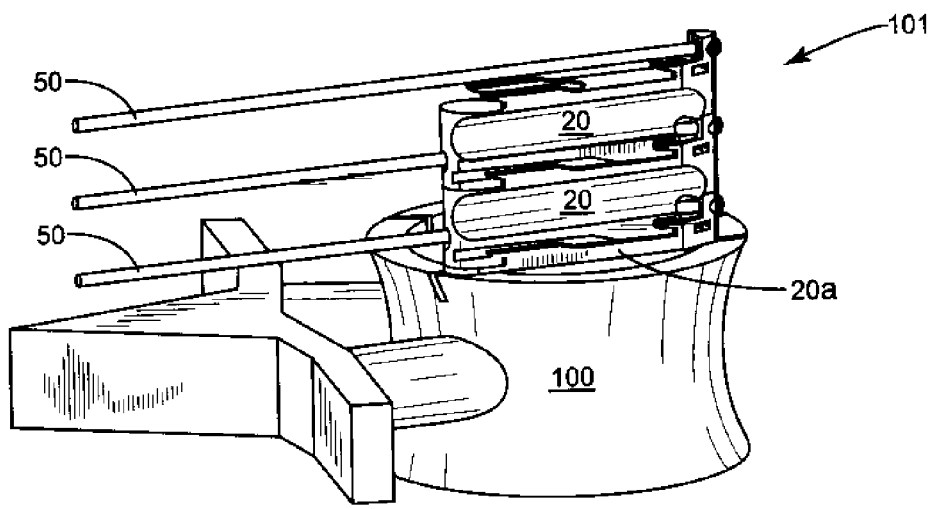
FIG. 14 is a perspective view of a third shim inserted in an intervertebral space according to one embodiment.

FIG. 14 illustrates another subsequent shim 20, referred to as third shim 20, interlocked in a stacked orientation with the previously-inserted second shim 20 and the end shim 20a. The third shim 20 is inserted along the guide 50 of the second shim 20 in a similar manner as previously explained above. Further, the locking mechanisms of the second and third shims 20 engage together as the third shim 20 is moved laterally into the intervertebral space 101 relative to the second shim 20. Once positioned in the stacked orientation, the end shim 20a, and second and third shims 20 are locked together.

Figure 15:
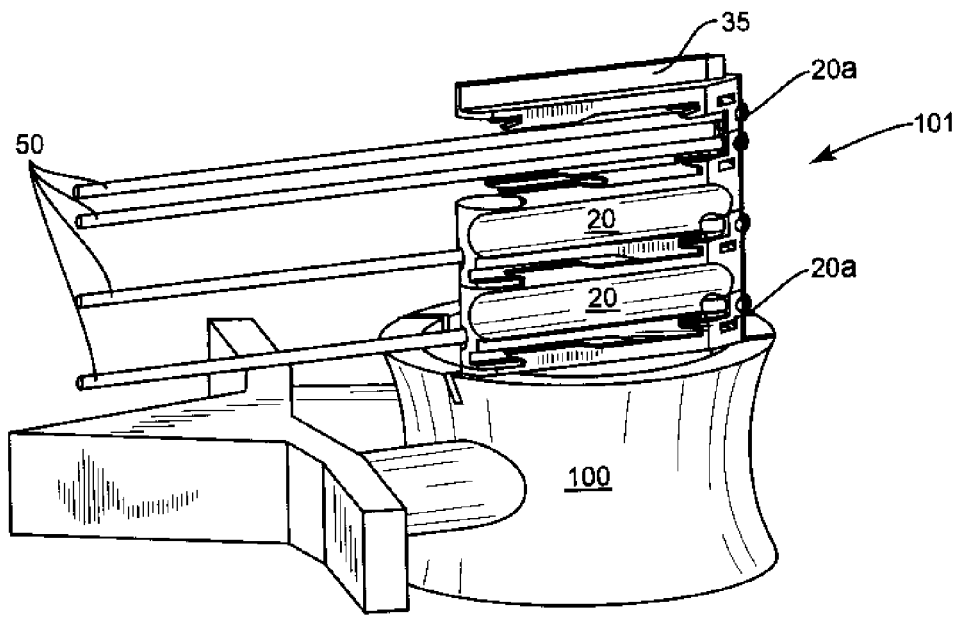
FIG. 15 is a perspective view of a second end shim inserted in an intervertebral space according to one embodiment.

FIG. 15 illustrates a second end shim 20a inserted into the intervertebral space 101 to contact the superior vertebral member (for clarity, the superior vertebral member is removed in FIG. 15). The second end shim 20a includes a first side with a keel 35 that fits in a trough in the superior vertebral member. The second end shim 20a further includes a second side that faces inward into the intervertebral space 101 and towards the first vertebral member 100. A guide 50 is attached to the second end shim 20a. The guide 50 includes a length to extend outward from the intervertebral space 101. Once inserted, a gap is formed between the second end shim 20a and the third shim 20. Further, two guides 50 are positioned in the gap as a first guide 50 extends outward from the second end shim 20a, and a second guide 50 extends from the third shim 20.

Figure 16:
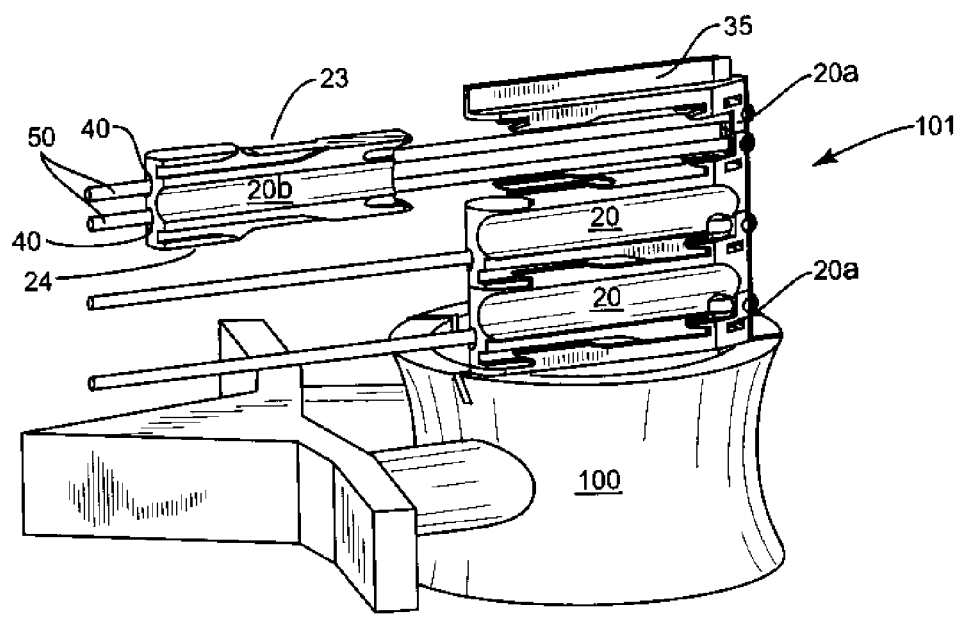
FIG. 16 is a perspective view of a subsequent shim being inserted in an intervertebral space according to one embodiment.

FIG. 16 illustrates the next shim 20b being inserted into the intervertebral space 101. The shim 20b includes a pair of passages 40 that extend along at least a section of the length of the shim. The first passage 40 is positioned to receive the guide 50 that extends outward from the second end shim 20a. The second passage 40 is positioned to receive the guide 50 from the third shim 20. During insertion, shim 20b is mounted onto the guides 50 and then laterally moved along the guides 50 and into the intervertebral space 101. A height of the shim 20b is determined to fit in the gap, and for the first side 23 to engage with the second end shim 20a, and the second side 24 to engage with the third shim 20. Further, locking mechanisms may be arranged on the first and second sides 23, 24 to interlock the shim 20b with the second end shim 20a and third shim 20 to prevent further movement. In one embodiment, shim 20b includes a single passage 40 that is sized to receive both guides 50.

The method illustrated in FIGS. 7-17 include the second end shim 20a being inserted at a time after several intermediate shims 20 are inserted into the intervertebral space 101. In another embodiment, the end shims 20a are each initially inserted into the intervertebral space 101. The intermediate shims 20 are then inserted between the end shims 20a.

FIG. 1 illustrates an embodiment with the shim 20b full inserted into the intervertebral space 101 and engaged with the second end shim 20a and third shim 20. The shims 20a, 20, 20b are each in a stacked orientation and extend across the height of the intervertebral space 101. The shims 20a, 20, 20b are interlocked together forming a unitary device 10 with structural integrity to space apart the vertebral members 100.

Figure 17:
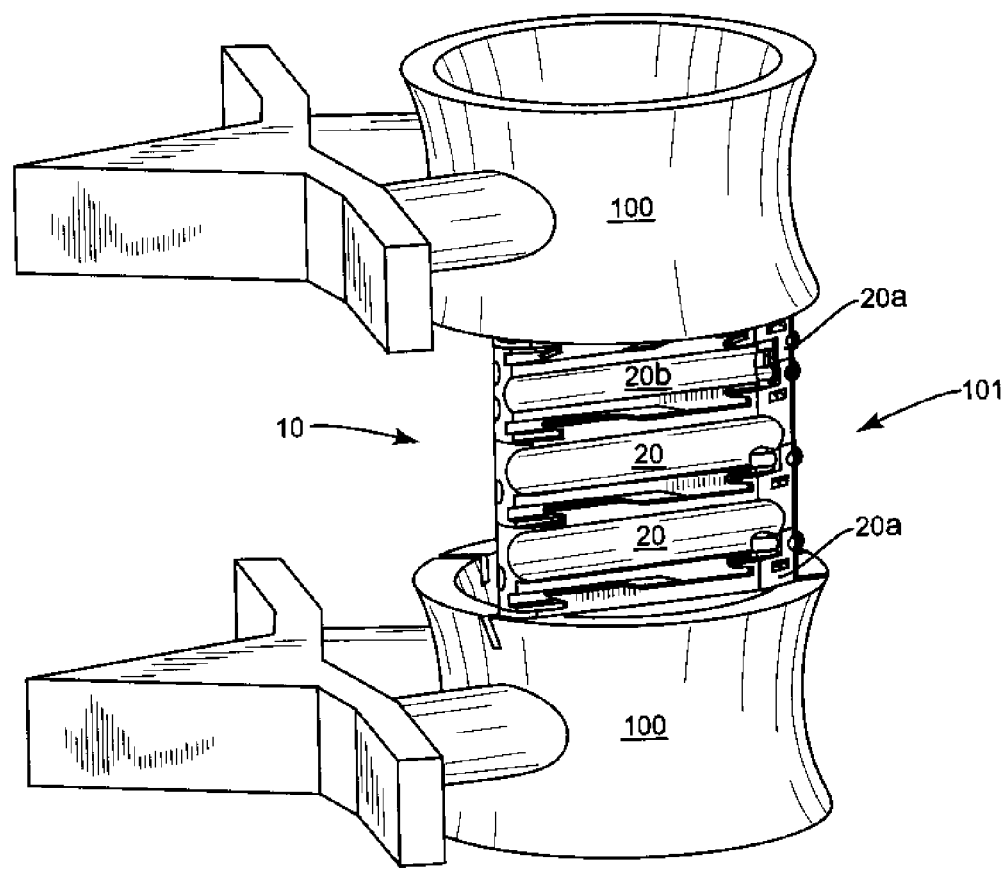
FIG. 17 is a perspective view of a device in an intervertebral space according to one embodiment.

At some point after the shims 20 are inserted, the guides 50 may be removed. In the methods described above, the guides 50 remain attached to the shims 20a, 20 until each of the device 10 is fully constructed in the intervertebral space 101. The guides 50 are then removed with the shims 20 remaining in the intervertebral space 101 as illustrated in FIG. 17.

In one embodiment, the guides 50 are removed from each of the shims 20a, 20 after they have been used to guide the subsequent shim 20 to the intervertebral space 101. By way of example, a guide 50 remains attached to a first shim 20 until the second shim 20 has been inserted. Once inserted, the guide 50 may be removed from the first shim 20. In one embodiment, the guides 50 are attached to the shims 20 after the shims 20 are inserted into the intervertebral space 101.

In the embodiments illustrated in FIGS. 7-17, the device 10 includes end shims 20a on the outer extents to contact the vertebral members 100. In one embodiment, end shims 20a are not used with the device 10. Rather, the first or second sides 23, 24 of the shims 20 are placed into contact with the vertebral members 100. In one embodiment, one or both of the sides 23, 24 include an enlarged width to increase the contact area between the shims 20 and the vertebral members 100.

Figure 18:
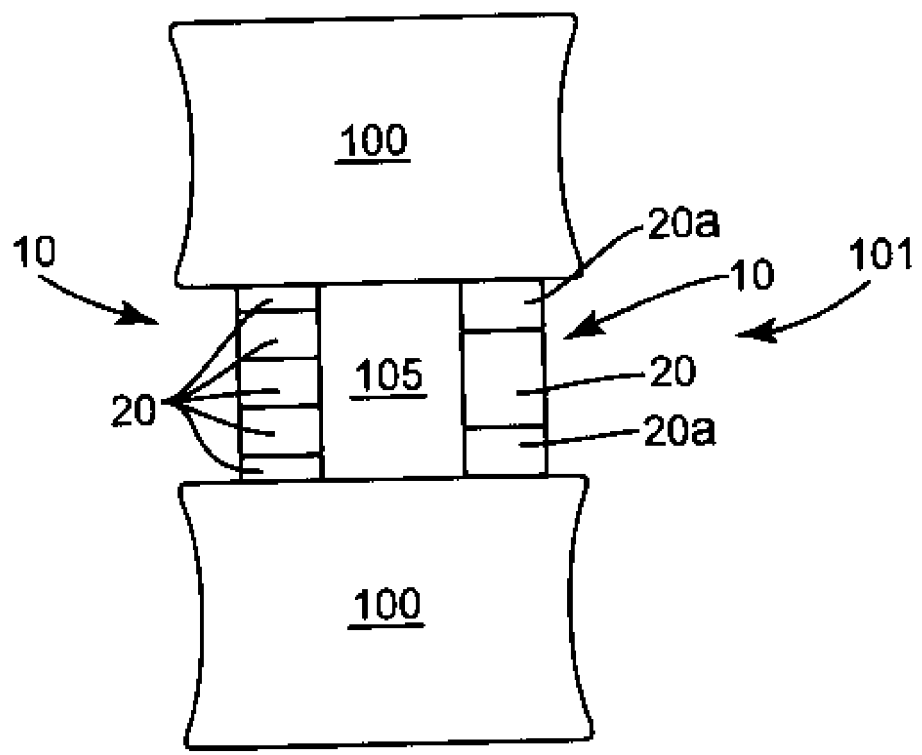
FIG. 18 is a perspective view of a pair of devices in an intervertebral space according to one embodiment.

The device 10 may include a variety of widths to fit in the intervertebral space 101. In one embodiment as illustrated in FIG. 18, a pair of devices 10 are positioned in the intervertebral space 101. The devices 10 are spaced apart with a space 105 formed therebetween. In one embodiment, the space 105 is sized to contain bone-growth material. In one embodiment as best illustrated in FIGS. 11B, 12B, and 13B, the lateral sides 25 of the shims 20 are scalloped with a central section of the shim 20 including a smaller width than the end sections. This shape provides for additional space to receive bone-growth material. In another embodiment, a single device 10 is positioned in the intervertebral space 101.

The device 10 may further be used as a distraction instrument to space apart the vertebral members 100. The individual shims 20, 20a, 20b may be inserted to increase an overall height H of the device 10 to be greater than the height of the intervertebral space 101. In one embodiment, outer shims 20, 20a may initially be inserted into the intervertebral space 101, and interior shims 20, 20b are subsequently added that expand the height H of the device 10 and the height of the intervertebral space 101 as necessary. In another embodiment, a separate distraction instrument is used to distract the vertebral members 100 prior to insertion of one or more of the shims 20, 20a, 20b into the intervertebral space 101.

In the methods described in FIGS. 7-17, the intervertebral space 101 is accessed through a posterior approach. Other applications contemplate other approaches, including anterior, postero-lateral, antero-lateral and lateral approaches to the spine. Further, the device 10 and methods may be used on various sections of the spine, including the cervical, thoracic, lumbar and/or sacral portions of the spine.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The surface of the shims 20, 20a, 20b may include treatments that facilitate and encourage bony ingrowth. Further, openings may extend through the shims 20, 20a, 20b to further facilitate bony ingrowth. The openings may extend cross-wise between the lateral sides 25, between the first and second sides 23, 24, or combinations thereof. In one embodiment, the end shims 20a include teeth to engage with the vertebral members 100. The teeth may be used in combination with the keel 35, or may be used without the keel 35. The present embodiments are, therefore, to be considered in all respects as illustrative and not restrictive, and all changes coming within the meaning and equivalency range of the appended claims are intended to be embraced therein.

What is claimed is:

1. An implant for spacing vertebral members comprising:
   a first shim with a distal end and an opposing proximal end;
   a guide rod with an elongated shape with a distal end and an opposing proximal end, the distal end of the guide rod mounted at the distal end of the first shim, the guide rod having a greater length measured between the distal and proximal ends than the first shim with the proximal end of the guide rod proximally extending outward beyond the proximal end of the first shim;
   a second shim stacked on the first shim, the second shim having a longitudinal passage that is fully circumferentially enclosed by the second shim, wherein the second shim includes a second guide rod mounted at a distal end of the second shim, the second guide rod including a greater length measured between its distal and proximal ends than the second shim with the proximal end of the second guide rod proximally extending outward beyond a proximal end of the second shim;

the guide rod disposed in the passage and extending entirely therethrough.

2. The implant of claim 1, wherein the distal end of the guide rod includes threads that engage with corresponding threads in the first shim.

3. The implant of claim 1, wherein the first shim includes a contact surface that contacts against the second shim when the guide rod is disposed in the passage, the contact surface being vertically offset from the guide rod.

4. The implant of claim 1, wherein the guide rod includes a smaller cross-sectional area than the passage.

5. The implant of claim 1, wherein the first shim includes opposing first and second vertical sides with a keel positioned at the first vertical side and the guide rod positioned at the second vertical side.

6. The implant of claim 1, wherein a length of the first shim measured between the distal and proximal ends is the same as a length of the second shim between the distal and proximal ends.

7. An implant for spacing vertebral members comprising:
a first shim extending along a first longitudinal axis from a proximal end to a distal end, the first shim having a first center between the ends, the first shim also having a first pair of ramps separated by a receptacle;
a second shim extending along a second longitudinal axis from a proximal end to a distal end, the second shim having a second center between the ends, the second shim also having a second pair of ramps;
the second shim configured to slide within the receptacle relative to the first shim between first and second configurations, the first configuration including the second center located distally of the first shim proximal end and disposed relatively farther from the first shim distal end, the second configuration including the second center located relatively closer to the first shim distal end, wherein the first pair of ramps is in sliding engagement with the second pair of ramps in the first configuration and spaced from contact with the second pair of ramps in the second configuration; and
wherein the sliding engagement urges the shims toward one another so that a distance measured between the longitudinal axes is smaller in the second configuration than in the first configuration.

8. The implant of claim 7, wherein the first pair of ramps are spaced longitudinally away from the proximal end of the first shim and have a length measured along the first longitudinal axis that is shorter than the first shim.

9. The implant of claim 7, wherein the second pair of ramps are spaced between the proximal and distal ends of the second shim.

10. The implant of claim 7, wherein the receptacle is formed between opposing rails that extend between the distal and proximal ends of the first shim and the second shim includes lateral wings that engage with the rails.

11. The implant of claim 7, wherein the first shim includes a guide rod mounted to the distal end and the second shim includes a longitudinal passage formed within an interior of the second shim, the guide rod positioned in the passage in the second configuration.

12. The implant of claim 11, wherein the guide rod is longer than the first and second shims and extends outward beyond the proximal ends of the first and second shims.

13. The implant of claim 7, wherein each of the first and second shims include guide surfaces that face each other in both the first and second configurations, the guide surfaces being in contact in the second configuration.

14. An implant for spacing vertebral members comprising:
a first shim with a distal end and an opposing proximal end with a first longitudinal axis extending through the ends;
a guide rod with an elongated shape with a distal end and an opposing proximal end, the distal end of the guide rod mounted at the distal end of the first shim, the guide rod having a greater length measured between the distal and proximal ends than the first shim with the proximal end of the guide rod proximally extending outward beyond the proximal end of the first shim;
a second shim having a distal end and a proximal end, the second shim having a longitudinal passage that is fully circumferentially enclosed by the second shim, the second shim also including a contact section;
the guide rod disposed in the passage and extending entirely therethrough;
the second shim being configured to longitudinally slide relative to the first shim and along the guide rod between a first configuration with the second shim positioned on the first shim by a first amount and a second configuration with the second shim positioned on the first shim by a larger second amount, a distance measured between the longitudinal axes being smaller in the second configuration than in the first configuration wherein each of the first and second shims include ramps that face towards each other and are configured to contact in the first configuration and be spaced apart in the second configuration.

15. The implant of claim 14, wherein the distal ends of the first and second shims align in the second configuration.

16. The implant of claim 14, wherein the distal end of the guide rod includes threads that engage with corresponding threads in the first shim.

17. The implant of claim 14, wherein the first and second longitudinal axes are parallel in the second configuration.

* * * * *